United States Patent [19]

Stout

[11] Patent Number: 4,883,662

[45] Date of Patent: Nov. 28, 1989

[54] METHOD OF INCREASING NATURAL KILLER CELL POPULATION OF CANCER PATIENTS

[75] Inventor: Robert L. Stout, Overland Park, Kans.

[73] Assignee: Clinical Biotechnologies, Inc., Kansas City, Mo.

[21] Appl. No.: 872

[22] Filed: Jan. 6, 1987

Related U.S. Application Data

[63] Continuation of Ser. No. 818,779, Jan. 13, 1986, abandoned, which is a continuation-in-part of Ser. No. 598,744, Apr. 10, 1984, Pat. No. 4,572,834.

[51] Int. Cl.$^4$ .................. A61K 39/42; A61K 39/395; A61K 35/16; A61K 37/02
[52] U.S. Cl. .................. 424/101; 424/85.2; 424/86
[58] Field of Search .................. 424/85-93,101, 424/85.2, 86

[56] References Cited

U.S. PATENT DOCUMENTS

| | | | |
|---|---|---|---|
| 4,572,834 | 2/1986 | Stout | 424/86 |
| 4,687,665 | 8/1987 | Stout | 424/86 |
| 4,689,222 | 8/1987 | McMichael | 424/88 |
| 4,690,915 | 9/1987 | Rosenberg | 424/101 |
| 4,692,332 | 9/1987 | McMichael | 424/88 |

FOREIGN PATENT DOCUMENTS 0089062  9/1983  European Pat. Off. .

*Primary Examiner*—Shep K. Rose
*Attorney, Agent, or Firm*—Hovey, Williams Timmons & Collins

[57] ABSTRACT

An in vivo method is described for increasing the population of Natural Killer (NK) cells in the blood of patients suffering from cancer, such NK cells having known activity against tumor cells. The method broadly involves injecting a specially prepared biologic into the patient's bloodstream and allowing the biologic to activate the patient's immune system so as to achieve a desired NK cell population increase (preferably at least a twofold increase). The biologic is produced by injecting an animal such as a goat with a virus (preferably a normally immunosuppressive Parvovirus) and allowed to react to the virus for a period of time to generate the biologic in its blood serum; blood is then withdrawn from the animal and the serum fraction thereof, containing the desired biologic, can be used in fractionated or more highly purified form.

4 Claims, 1 Drawing Sheet

FIRST STAGE CHROMATOGRAPHY PROFILE

SECOND STAGE CHROMATOGRAPHY PROFILE

THIRD STAGE CHROMATOGRAPHY PROFILE

METHOD OF INCREASING NATURAL KILLER CELL POPULATION OF CANCER PATIENTS

This is a continuation of application Ser. No. 818,779, filed 1/13/86, now abandoned, which is a continuation-in-part of Ser. No. 598,744, filed 4/10/84, now U.S. Pat. No. 4,572,834.

BACKGROUND OF THE INVENTION

1. Field of the Invention

The present invention is broadly concerned with an in vivo method for increasing the natural killer cell population in the peripheral blood of human patients, and especially patients suffering from cancer. More particularly, it is concerned with such a method which involves administering to such patients a biologic preferably derived by viral immunization of an animal such as a goat, and recovery of the biologic from the animal's blood. Advantageously, the goat or other test animal is treated with a virus such as a parvovirus which is normally immunosuppressive in a permissive host.

2. Description of the Prior Art

Vaccines have been in use since Edward Jenner (1749–1823) first recognized that people exposed to non-virulent strains of microorganisms could be protected against infection by the related virulent strains. His vaccination of patients with exudate of cowpox sores provided those same patients with partial protection against smallpox. Numerous vaccines have subsequently been prepared and used in both humans and animals. Immunization has been accomplished by vaccination with a suspension of live, attenuated, or killed organisms or specific protein, glycoprotein or surface material from various bacteria, rickettsiae, or viruses. These would include vaccines against anthrax, rabies, typhoid, cholera, smallpox, measles, mumps, pertussis, plague, and polio. The vaccine in each case has been intended to provide protection against a specific pathogen. While vaccination may provide long term specific protection it may or may not produce short term immunosystem modulation. The immune system responds to challenge via vaccination or infection by increased activity. This may result in the short term production of antigen non-specific immunoregulatory modulators such as interferon, interleukins, and other various lymphokines.

The rationale for a system that becomes active only in response to a specific challenge is simple. If the immune system operated at a high pitch of activity all the time, it would age prematurely and no longer provide the systematic protection it was evolved to deliver. Another possible complication with an unusually active immune system could be the initiation of autoimmune reactions in which the system starts acting against itself, resulting in the destruction of normal tissue. Arthritis is exemplary of this particular condition.

Increased activity of the immune system by virtue of improper regulation could furthermore result in an inability to elicit an appropriate response. As an example, a massive response to a splinter in a finger would be completely inappropriate, just as no response to a major infection would be equally inappropriate.

Immunomodulation may provide a regulatory-directed approach at a self-healing, particularly with respect to such intractable diseases as cancer. For this to occur to minimal criteria must be met. The immune system must be sufficiently intact to respond to the regulator(s), and secondly, the system under appropriate stimulation must have T-cells, B-cells and Natural Killer cells present that are capable of responding to the target antigen(s) or cell(s). In such an instance, however, a nonspecific immunomodulator could potentially serve to "turn on" the immune system and initiate healing.

A number of immunomodulators have previously been isolated and described and these appear to belong to one of three general groups, namely the interferons, the interleukins and the corticosteroids and leukotrienes.

The interferons are a family of glycoproteins normally produced in response to a viral infection and are produced by leukocytes and fibroblasts. There are three main types, alpha, beta and gamma. They have molecular weights in the range of 15,000 to 40,000 daltons. Recently they have been produced by recombinant DNA techniques. The interferons have been found to have an absolute specie specificity, and are only effective in the specie that produced it.

The second group of immunomodulators are the interleukins. They are a family of glycoproteins that are produced by white cells. It is believed that the lymphokines cause the activation of Natural Killer cells and B-cells, and act in the initiation and propagation of the specific sequences of cellular interactions that are not recognized as the immune response. These growth promoters and activators participate in the generation of immunoreactive cells. The lymphokines are antigen non-specific in that they activate all T and B cells in anticipation of the presentation of an antigen or a cell. The apparent molecular weights are in the range of 15,000 - 50,000 daltons. To date, treatment protocols for cancer patients involving interleukins have been of an in vitro character, i.e., blood is withdrawn from the patient, treated in vitro, and returned to the patient. This is a relatively cumbersome process and is subject to all of the typical problems attendant to in vitro, as opposed to in vivo, procedures.

The third type of regulators are the corticosteroids and the leukotrienes, which act as regulators in inflammation. When produced in atypical amount, the leukotrienes can cause immediate type hypersensitivity and anaphylaxis. They are principally oxygenated products of archidonic acid. In contrast the corticosteroids and leukotrienes are small molecular weight compounds in comparison to the interleukins and interferons.

All of the immunological regulators produced commercially are extracts or concentrates of tissue culture fluids from mitogen stimulated lymphoid and myleloid cells. The exceptions to this are interferons and IL-2 which have been produced by genetic engineering. The other immunological modulators that have been artificially produced are the interferons. The difficulty with each of these production methods is that the individual reagents being produced to not reproduce the plethoric effect seen in vivo. No practical method has heretofore been discovered to produce a plurality of the immunoregulators together in the same proportions as they would normally be produced in response to infection or cancer in situ. Additionally, the cost of prior known production methods has been considerable, thereby further limiting the utility of immunomodulators.

SUMMARY OF THE INVENTION

The present invention is broadly concerned with a unique method for significantly increasing the population of Natural Killer cells in the blood of human patients, and particularly those suffering from cancer. It has been established that increasing such Natural Killer cells is an important component of the immune system, and that accordingly the present method should be a decided advantage in cancer treatment. The method generally involves administering to the patient an amount of specially prepared biologic, and allowing the biologic to stimulate the patient's immune response and thus increase the Natural Killer cell population. Accordingly the method of the invention completely avoids in vitro treatment of the patient's blood.

The patient's immune system should, of course, be sufficiently intact to respond to the biologic; moreover, if a cure or amelioration of metastatic disease is to be achieved, the patient must have Natural Killer cells present which can respond to the metastasis. Furthermore, it is believed at least a two-fold increase in Natural Killer cells should be effected in order to obtain meaningful treatment results.

The biologic of the invention is advantageously obtained by a method which comprises the steps of injecting a virus such as a parvovirus into an animal, and permitting the injected animal to react to the presence of the virus for a period of time in order to develop in the animal's blood serum biologic in sufficient quantity and/or activity that 50 microliters of the animal's serum, when added to an in vitro human white blood cell culture containing $2-4 \times 10^5$ white blood cells and followed by 3 days incubation at 37° C. under a 5% $CO2/95\%$ air atmosphere, will give rise to at least about a 50% increase in T-helper and Natural Killer cells in the biologic-supplemented cell culture, as compared with an otherwise identical and identically cultured in vitro cell culture having added thereto 50 microliters of serum from a normal animal of the same species as the injected animal. The final step in the method involves recovering serum from the injected animal which contains the desired biologic.

In particularly preferred forms the animal in question is a goat, and the virus injected is a Parvovirus of a type which is immunosuppressive in a normal permissive host animal (e.g., a cat or dog) for the Parvovirus. Thus, in the presently preferred method of the invention, use is made of a normally immunosuppressive virus in a non-permissive host for the virus; quite surprisingly however, this serves to develop an immunostimulative biologic in the injected animal's serum which has the salutory effects outlined above.

In other forms of the invention, the injected animal can be selected from the group consisting of goats, horses, sheep, rabbits and monkeys, with the period of time after injection of the virus being at least about one month.

The injected and immunized animal's serum can be used in relatively crude form, such as after only conventional ammonium sulfate fractionation. In other instances, however, the fractionated serum is subjected to further isolation procedures, in order to substantially purify the biologic.

In actual practice, a number of test goats are normally immunized with Parvovirus, and the serum of these goats is tested after an appropriate time (e.g., about 3 months) for the presence of biologic using the standard outlined above. those animals which are positives, i.e., their serum exhibits the biologic in the manner defined, are then bled and their serum, containing the biologic, is recovered.

BRIEF DESCRIPTION OF THE DRAWINGS

FIGS. $1 \geqq 3$ are respectively chromatography profiles developed as a result of first stage, second stage and third stage column chromatographies of ammonium sulfate fractionated Parvovirus-immunized positive goat serum in accordance with the preferred method of producing the biologic of the invention.

DESCRIPTION OF THE PREFERRED EMBODIMENTS

Figure 1:
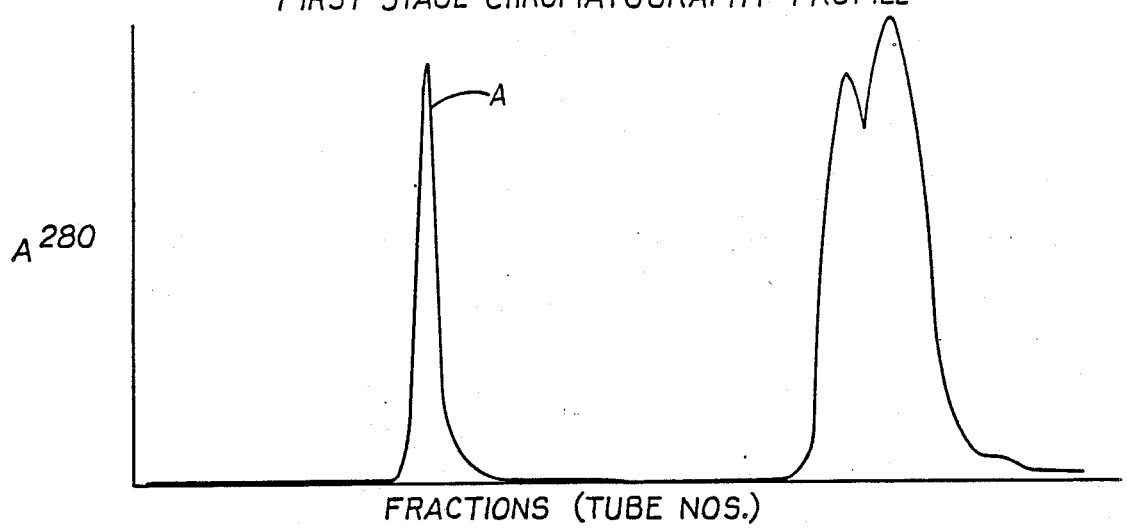

The following examples set forth the most preferred method of producing biologic in accordance with the invention.

EXAMPLE I

This Example sets forth the preferred procedures for the production and recovery of the biologic of the present invention.

Goat Vaccination

A total of five normal goats were initially hypervaccinated with Parvovirus in multiple sites on their dorsal rear halves, using a total of 1 cc. of commercially available Feline Pan Leukopenia vaccine (Dellen Laboratories, Inc., Westwood, Maine). Thereafter, at intervals of about one and two months after the initial injection, each goat was again injected with 1 cc total quantities of Canine Origin Parvovirus vaccine (Fromm Laboratories, Inc., Grafton, Wisconsin or Duramune Vaccine, Temple, Texas. At the end of about three months from the date of the initial injection, a sample of whole blood was withdrawn from the carotid artery of the neck of each goat, and the samples treated as hereinafter described.

Goat Plasma Preparation

The goat blood samples were separately centrifuged (about 500 ml. at a time) using a swinging bucket rotor centrifuge operated at 2000 rpm for 45 minutes to pellet the red blood cells. The plasma was then removed from the packed red cells in each sample, and volumetrically measured. an absorbance reading (280 nm) of each plasma sample diluted 1:50 with PBS (pH 7.5) was then taken for record purposes.

Serum Preparation

Reagents Employed:

1.0 molar calcium Chloride 14.7 gm $CaCl_2 2H_2O$ in 100 ml distilled water

Thrombin

Miles Laboratories, Inc.

Bovin Thrombin (500 units/ml)

Reconstitute vial with:

1.0 ml sterile saline 1.0 ml glycerol

Saline 9 gms Sodium Chloride in 100 ml distilled water

Procedure:

Use 1.0 ml of 1. molar calcium chloride for each 100 ml of plasma.

Use 100 ul of thrombin for each 100 ml of plasma.

1. The required amount of calcium chloride and thrombin was added to each measured plasma sample in a beaker.

2. The respective plasma/calcium chloride/thrombin mixtures were then stirred gently and thereafter each beaker was placed in a water bath at 37° C. for 30 minutes.

3. The beakers of clotted plasma were then removed from the water bath, and the plasma in each beaker cut up into small pieces.

4. Each mixture was then poured into a respective centrifuge tube, and the tubes were spun 10,000 rpm for 30 mintues.

5. Serum was then carefully removed from the clot at the bottom of each of the tubes to give separate serum samples.

6. The serum volume absorbance reading at 280 nm for each sample was then taken and recorded.

Biologic Determination

An in vitro assay was next performed on the serum samples derived from each of the test goats, in order to determine which of the goats produced the desired biologic in sufficient quantity. Normal human white cells were first cultured in RPMI-1640 media (a standard tissue culture media produced by K.C. Biological of Lenexa, Kansas) supplemented with 10% fetal calf serum. Fifty microliters of each of the goat test serums produced as described previously were then added to respective cultures each containing $2\text{-}4 \times 10^5$ cultured human white blood cells in a total volume of 2 ml. The cultures, with goat serum added, were then incubated in an atomsphere of 5% $CO_2$/95% air at 37° C. for 3 days. Each separate culture was then stained with two types of fluorescent-labeled monoclonal antibodies respectively specific against T-helper cells (OKT-4 monoclonal antibody sold by Ortho Diagnostic of Raritan, New Jersey) and Natural Killer cells (LEU-7 monoclonal antibody sold by The Becton-Dickinson Co. of Mountain View, California). The strainings were performed following the supplier's directions, and after about one hour, the stained samples were analyzed using a flow cytometry device, namely a model 50H cytofluorograph (Ortho Instruments, Westwood, Mass.) to count both T-helper and Natural Killer cells in each culture. The test animal serums were compared against a stained and counted control sample comprising cultured human white blood cells and 50 microliters of normal goat shich exhibited as outlined at least about a 50% increase in the number of T-helper cells and Natural Killer cells, as compared with the control, were considered positives for the biologic of the invention. In this specific test three of the five goat serum samples gave positive results; one sample gave about a 50% increase, whereas the other two samples gave an increase on the order of 125%.

The above described in vitro determination assay is used throughout the purification and isolation protocol in order to identify which of the separated fractions in each instance contained the desired biologic.

The three positive serum samples were each further treated as described below (the procedure for only a single serum sample is set forth, but the method of treating all the smples was the same). In this example, the respective positive serum samples were treated separately; however, such samples could be pooled if desired.

Ammonium Sulfate Fractionation

Reagents Employed:

Ammonium Sulfate (Sigma S-5182, Sigma Chemical Co., St. Louis, Missouri)

0.01m Sodium Phosphate (pH 7.6)

Procedure:

1. 24.3 gm of ammonium sulfate was weighed out for each 100 ml of serum to be fractionated.

2. The serum sample was placed in a beaker and stirred. During stirring small amounts of ammonium sulfate were added, making sure that all was dissolved before adding more ammonium sulfate; this procedure was continued until entire amount of ammonium sulfate was added to the sample. The sample was then gently stirred for another 30 minutes.

3. The serum sample was then placed in a centrifuge tube and spun at 10,000 rpm for 30 minutes, whereupon supernatant was carefully removed from the pellet. The supernatant serum fraction was tested for the presence of the desired biologic using the in vitro cell culure assay described above under "Biologic Determination" and was found to be negative;

this supernatant was therefore discarded.

4. The centrifuged pellet from step 3 was then redissolved in 0.01m sodium phosphate (pH 7.6), with the final volume of redissolved pellet being the same amount as that of original serum volume.

5. Steps 2 and 3 were then repeated for the serum sample, in order to effect another separation; again, the in vitro determination assay confirmed that the supernatant did not contain the desired biologic.

6. The pellet was then redissolved to one-half of the original serum volume, using 0.01 M sodium phosphate (pH 7.6).

7. The resuspended material sample was then placed into a section of 12,000 mw cut-off dialysis tubing.

8. The sample was then dialyzed against .01 M sodium phosphate (pH 7.6), using three changes of 4 liters in the dialysis.

9. The sample was then removed from the dialysis tubing and put into a centrifuge tube.

10. The tube was next spun at 10,000 rpm for 30 minutes.

11. The supernatant from the centrigue tube was then removed and the volume measured and recorded; another in vitro determination assay as described above was performed on the supernatant, to confirm that it did contain the desired biologic.

12. The absorbance at 280 nm for the supernatant was taken and recorded.

13. The supernatant material resulting from the fractionation of the sample was stored in a sterile bottle.

First Stage Chromatography (using DE-52 anion exchange resin, Whatman, Inc., Clifton, N. J.)

1. An appropriate quantity of DE-52 resin was swelled and equilibrated in 0.01 molar Sodium Phosphate, pH 7.6

2. A column (4.4 cm x 83 cm) was packed with swelled DE-52 resin. The column was washed with 2 liters of 0.01 M $NaH_2PO_4$ (pH 7.6) at 75 cm pressure.

3. 40 ml of the ammonium sulfate fractionated serum from the sample were loaded onto the DE-52 column at the same pressure as the wash. The material was then eleuted with 0.01 M $NaH_2PO_4$ (pH 7.6) wash.

4. Liquid from the column was collected in separate tubes (150 drops/tube--approximately 5.0 ml) until all protein fractions were completely eluted. About 1.0 liter of .01 molar $NaH_2PO_4$ was passed through the column.

5. The column was then washed with 1.5 liters of 0.01 molar $NaH_2PO_4$ containing 0.5 m NaCl (pH 7.6) to remove bound material from the column. Liquid from the columns was collected in separate tubes (150 drops/tube) until the buffer was expended.

6. The absorbance at 280 nm was taken for all tubes collected. A plot of absorbance ($A^{280}$) vs. tube number was prepared to locate the peaks. This graph is reproduced as FIG. 1.

7. The material within tubes located in each separate peak off the plot were then pooled and assayed using the described in vitro determination assay.

8. The pooled material from the first peak (peak A of FIG. 1) was found to contain the biologic of the invention. This material was concentrated by placing the material into a section of dialysis tubing and tying off the ends; the tubing was then placed into a tub of polyethylene glycol (20,000 mw, Sigman Chemical Co., St. Louis, Missouri) and concentrated to about 10% of the original pooled volume. The tubing was then rinsed well with water.

9. The pooled material within the tubing was then dialyzed against PBS (pH 7.5). Three changes of 4 liters were used to remove polyethylene glycol and salt.

10. The dialyzed material was then removed from tubing and the volume measured. Absorbance readings at 280 nm were taken and recorded along with volume.

Second Stage Chromatography (using S-200 size exclusion chromatography resin, Sigma Chemical Co., St. Louis, Missouri)

1. An elution column (4.4 cm x 83 cm) was packed and equilibrated with S-200 resin, and the column was washed with 2 liters of PBS (0.2 M $NaH_2PO_4$ containing 0.15 m NaCl, pH 7.5) at 60 cm. pressure.

2. 15 mls. of the pooled, dialyzed material from the first concentrated peak (peak A, FIG. 1) off of the DE-52 column was next loaded onto the S-200 column, and the sample was eluted using the PBS of step 1. The liquid off the column was collected in separate tubes (100 drops/tube, approximately 3.0 ml).

Figure 2:
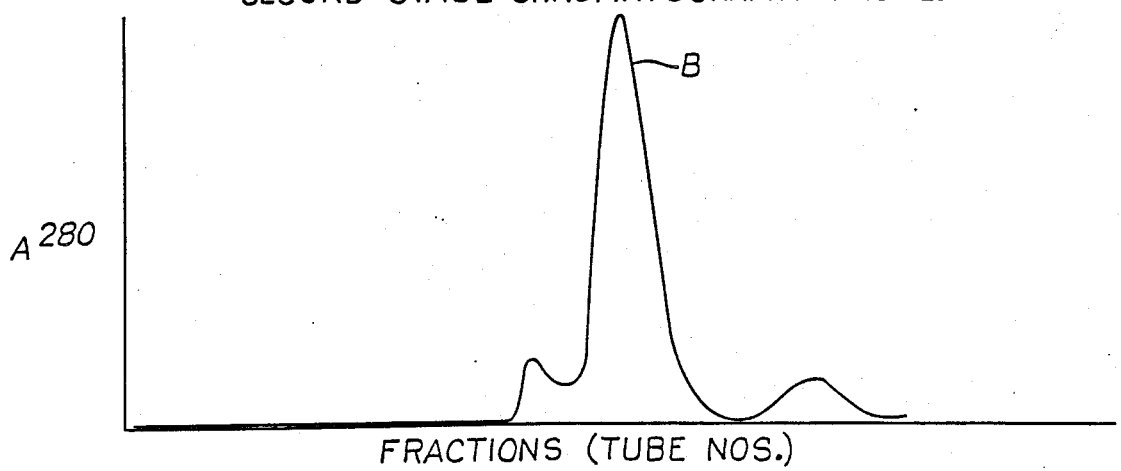

3. Absorbance readings at 280 nm were then taken for all of tubes collected. A plot of $A^{280}$ vs. tube number was then prepared; this plot is reproduced as FIG. 2.

4. The material within tubes located in each peak were pooled and concentrated with polyethylene glycol as set forth in steps 7 and 8 of the first stage chromatography procedure. The pooled samples were each then tested using the in vitro determination assay.

5. The pooled material from the largest peak (peak B, FIG. 1) was found to contain the biologic. This material was then dialyzed using dialysis tubing against 3 changes of 4 liters of PBS (0.01 M $K_2HPO_4$ containing 0.15 M NaCl, pH 7.5).

6. The dialyzed material was then removed from the tubing and the volume measured and recorded. An absorbance ($A^{280}$) was then taken on the dialyzed material, and the reading recorded.

Third Stage Gel Chromatography (using CM Blue AFFI gel cation exchange resin, Bio-Rad Corp., Richmond, California)

1. A column (1.5 cm x 38 cm) was packed and equilibrated with the CM Blue AFFI gel, and the column was washed with 2 liters of 0.01 M $K_2HPO_4$ containing 0.15 M NaCl, pH 7.25, at 45 cm pressure.

2. 8 ml of material concentrated from the largest peak off the S-200 column (peak B, FIG. 2) was then loaded onto the column.

3. The column was then washed with 0.01 M $K_2KPO_4$ containing 0.15 M NaCl (pH 7.25) until all peaks were eluted, using approximately 150-200 ml PBS for the column. Liquid off the column was collected in separate tubes (90 drops/tube, about 2 ml).

4. The column was again washed with 100 ml of .01 M $K_2HPO_4$ containing 0.5 m NaCl (pH 7.25 to further elute the bound material; liquid from the column was collected in tubes (90 drops/ tube).

Figure 3:
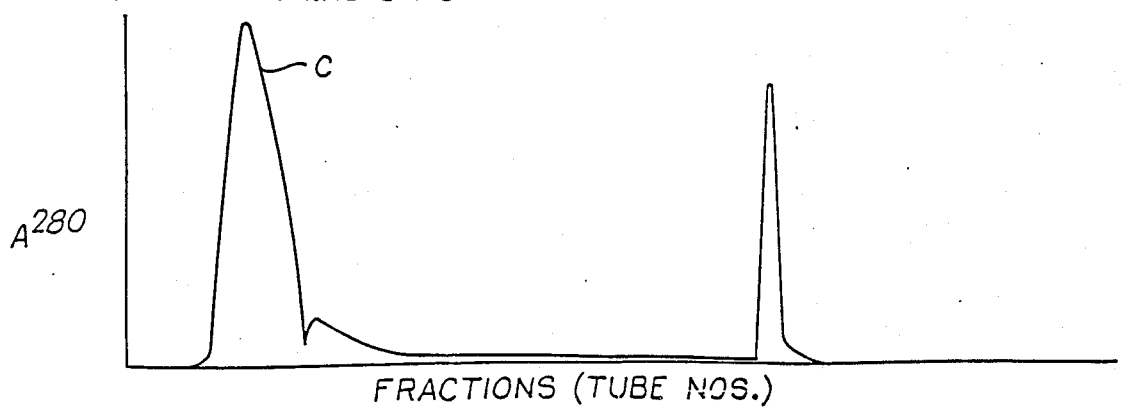

5. Absorbance readings at 280 nm were taken for all tubes and a plot of $A^{280}$ vs tube number from both elutions was prepared; this plot is reproduced as FIG. 3. Material within each peak was pooled, and these were assayed using the in vitro determination assay.

6. Material from the first peak (peak C, FIG. 3) was found to contain the biologic; this material was concentrated with polyethylene glycol as described above in the first stage chromatography procedure.

7. The concentrated material was next dialyzed against PBS, using three changes of 4 liters each.

8. The material was next removed from dialysis tubing. Absorbance at 280 nm was read and recorded.

9. The material was filtered using a 0.2 um filter and stored.

As is evident from the foregoing, after a determination is made for the positive serum samples (i.e., those containing adequate amounts of biologic) successive fractionation and separation techniques may be employed to obtain the relatively purified biologic material, with appropriate assays being performed on separated fractions in order to ensure that the biologic is retained throughout. The final biologic product comprises proteinaceous component(s) which have not to date been completely characterized. However, the product is presently believed to be an interleukin protein or proteins having an apparent molecular weight in the range of 100,000 to 120,000 daltons; the components also appear to be glycosylated. A sample of the purified biologic made in accordance with the present invention has been deposited with the American Type Culture Collection; such sample has been accorded accession number 40105. Obviously, however, there is no desire to be bound to any preliminary or partial characterizations, and such are offered only in an effort to disclose all presently available pertinent information.

While the above described separation and isolation procedures are in many cases preferred, it should be understood that the biologic product derived from the methods of the invention can be used without such purifications, particularly if used in connection with animals. In the latter case, the fractionated positive goat serum can be used, inasmuch as such a relatively crude material contains the desired proteinaceous component(s), while potentially interfering interleukins have been removed.

EXAMPLE II

EFFECT OF BIOLOGIC ON HUMAN CANCER PATIENT

A terminally ill cancer patient undergoing chemotherapy was treated with the purified biologic described in Example I. A whole blood sample was collected from the patient before her first treatment, and the patient was tested by intradermal challenge skin scratch test (50 ug) for hyper-reaction to the goat-derived biologic prior to treatment. The first course of therapy involved injection of fifty (50) micrograms of purified stimulant (diluted to a volume of 5 ml. in saline solution) given each day for three successive days, starting on Dec. 19. The saline/biologic was given by slow intravenous push. The patient was sampled again after the third treatment. The fourth and fifth treatments were identical and given on Jan. 4 and Jan. 5. On Jan. 6 the patient's blood was sampled. The samples were collected using a vaccutainer confaining EDTA. Thereafter, the patient was treated with 1 mg/5 ml injections on Jan. 4 and Jan. 6. The patient's condition continued to deteriorate and she was again treated (10 mg/ml) on April 10. On Apr. 13 the patient's blood was again sampled.

At the end of the therapy the patient had noted no unusual qualitative differences during the treatment period. However, the patient contained to deteriorate and died in June. The major change that occurred during treatment was a 3.5 fold increase in the patient's Natural Killer cell population. Historically, the Natural Killer population has been demonstrated to be active against virally injected cells and tumor cells. Accordingly, the biologic served as an immunostimulant in the patient.

TABLE I
TREATMENT OF HUMAN WITH PURIFIED BIOLOGIC

| Date | Biologic Saline | Sample | T-Helper | T-Suppressor | Natural Killer |
|---|---|---|---|---|---|
| | | | Lymphocyte (% of Each Population) | | |
| 12/19 | 50 ug/5 ml | X | 53.2 | 29.1 | 10.7 |
| 12/20 | 50 ug/5 ml | | | | |
| 12/21 | 50 ug/5 ml | X | 54.7 | 30.8 | 18.9 |
| 12/29 | — | X | 47.7 | 24.6 | 24.2 |
| 1/04 | 1 mg/5 ml | X | 50.8 | 29.3 | 25.8 |
| 1/06 | 1 mg/5 ml | X | 52.5 | 31.6 | 24.6 |
| 3/28 | — | X | 34.0 | 23.2 | 26.5 |
| 4/10 | 10 mg/10 ml | | | | |
| 4/13/ | — | X | 50.7 | 42.0 | 35.2 |

I claim:

1. An in vivo method of increasing the Natural Killer cell population in the blood of a cancer patient, said method comprising the steps of:

injecting a biologic into the bloodstream of said cancer patient, and allowing said biologic to operate therein for a period of time to increase said Natural Killer cell population, said biologic being a glycoprotein and having an apparent molecular weight of above about 100,000 and being derived from the blood of an animal injected with a virus, wherein the aminal's blood containing the biologic is fractionated to separate potentially interfering substances from the biologic, said virus being a feline panleukopenia or canine origin parvo virus and said animal being other than a feline or canine which is a nonpermissive host for the virus, said virus-injected animal being allowed to react to the presence of the virus such that 50 microliters of the animal's serum, when added to an in vitro human white blood cell culture containing $2-4 \times 10^5$ white blood cells and followed by three days incubation at 37° C. under a 5% $CO_2$/95% air atmostphere, will give rise to at least about a 50% increase in T-helper and Natural Killer cells in the biologic-supplemented cell culture as compared with an otherwise identical in vitro cell culture having added thereto 50 microliters of serum from a normal animal of the same species as said injected animal, such rise in T-helper and Natural Killer cells being detected by staining with fluorescent-labeled monoclonal antibodies against T-Helper and Natural Killer cells.

2. The mathod of claim 1, said increase in Natural Killer cells being at least twofold.

3. The method of claim 1, said animal being selected from the group consisting of goats, horses, sheep, rabbits and monkeys.

4. The method of claim 3, said animal being a goat.

* * * * *